US008604787B2

(12) United States Patent
Posse (10) Patent No.: US 8,604,787 B2
(45) Date of Patent: Dec. 10, 2013

(54) MAGNETIC RESONANCE SPECTROSCOPY WITH REAL-TIME CORRECTION OF MOTION AND FREQUENCY DRIFT, AND REAL-TIME SHIMMING

(75) Inventor: Stefan Posse, Albuquerque, NM (US)

(73) Assignee: Stefan Posse, Albuquerque, NM (US)

( * ) Notice: Subject to any disclaimer, the term of this patent is extended or adjusted under 35 U.S.C. 154(b) by 214 days.

(21) Appl. No.: 12/931,196

(22) Filed: Jan. 26, 2011

(65) Prior Publication Data
US 2011/0221439 A1 Sep. 15, 2011

Related U.S. Application Data (63) Continuation-in-part of application No. 11/789,633, filed on Apr. 24, 2007, now abandoned.

(60) Provisional application No. 60/795,381, filed on Apr. 27, 2006.

(51) Int. Cl.
G01V 3/00 (2006.01)

(52) U.S. Cl.
USPC .......................................................... 324/309

(58) Field of Classification Search
USPC ................................................. 324/300–322
See application file for complete search history.

(56) References Cited

U.S. PATENT DOCUMENTS

| 5,166,620 A | | 11/1992 | Panosh | |
|---|---|---|---|---|
| 5,657,758 A | * | 8/1997 | Posse et al. | 600/413 |
| 5,709,208 A | * | 1/1998 | Posse et al. | 600/410 |
| 5,879,299 A | * | 3/1999 | Posse et al. | 600/410 |
| 6,294,972 B1 | | 9/2001 | Jesmanowicz et al. | |
| 6,552,539 B2 | | 4/2003 | Uetake | |
| 2007/0252597 A1 | * | 11/2007 | Posse | 324/312 |

OTHER PUBLICATIONS

Posse, S., DeCarli, C.S., Le Bihan, D., Three-dimensional Echo-Planar MR Spectroscopic imaging at short echo times in human brain, Radiology 1994; 192, 733-738.
Posse S, Tedeschi G, Risinger R, Ogg R, Le Bihan D. High speed 1H spectroscopic imaging in human brain by echo planar spatial-spectral encoding. Magn Reson Med 1995;33(1):34-40.
Posses, Dager SR, Richards TL, Yuan C, Ogg R, Artru AA, Muller-Gartner HW, Hayes C. In vivo measurement of regional brain metabolic response to hyperventilation using magnetic resonance: proton echo planar spectroscopic imaging (PEPSI). Magn Reson Med 1997;37(6):858-865.

(Continued)

Primary Examiner — Dixomara Vargas (57) ABSTRACT

Disclosed are MR Spectroscopy and MR Spectroscopic Imaging (MRSI) methods comprising the sequential steps of water suppression, spatial prelocalization and spatial-spectral encoding, wherein the water suppression is modified to additionally measure and correct the frequency drift, the change in magnetic field inhomogeneity in the volume of interest, and the object movement. By inserting between the water suppression RF pulse and the dephasing gradient pulses either a phase sensitive MRI encoding module, or a 1D, 2D or 3D high-speed MRSI encoding module with simultaneous acquisition of the decaying water signal it is possible to measure frequency drift, magnetic field inhomogeneity and object movement. This information is used to dynamically change the synthesizer frequency of the scanner, the shim settings and to rotate the encoded k-space. In the preferred implementation this information is computed in real-time during the ongoing scan and via feedback loop downloaded to the acquisition control unit to update the aforementioned parameters before the subsequent data acquisition.

14 Claims, 5 Drawing Sheets (56) References Cited

OTHER PUBLICATIONS

Dager SR, Layton ME, Strauss W, Richards TL, Heide A, Friedman SD, Artru AA, Hayes CE, Posse S. Human brain metabolic response to caffeine and the effects of tolerance. Am J Psychiatry 1999;156(2):229-237.
Dager SR, Friedman SD, Heide A, Layton ME, Richards T, Artru A, Strauss W, Hayes C, Posse S. Two-dimensional proton echo-planar spectroscopic imaging of brain metabolic changes during lactate-induced panic. Arch Gen Psychiatry 1999;56(1):70-77.
Posse, S., Otazo, R., Caprihan, A., et al., Proton Echo Planar Spectroscopic Imaging of J-Coupled Resonances in Human Brain at 3 and 4 Tesla, Magn. Reson. Med. (2007), vol. 58, (2), 236-244.
Lin, F.-H., Tsai, S.-Y., Otazo, R., Caprihan, A., Wald, L.L, Belliveau, J.W., Posse, S., Sensitivity-encoded (SENSE) Proton-Echo-Planar-Spectroscopic-Imaging (PEPSI) in Human Brain, Mag. Reson. Med. (2007), vol. 57 (2), 249-257.
Posse S, Otazo R, Tsai SY, Yoshimoto AE, Lin FH. Single-shot magnetic resonance spectroscopic imaging with partial parallel imaging. Magn Reson Med. Mar. 2009; 61 (3), 541-547.
Scott AD, Keegan J, Firmin DN. Motion in cardiovascular MR imaging. Radiology. Feb. 2009;250(2):331-51.
Fu ZW, Wang Y, Grimm RC, Rossman PJ, Felmlee JP, Riederer SJ, Ehman RL Orbital navigator echoes for motion measurements in magnetic resonance imaging. Magn Reson Med. 1995;34:746-753.
Ward HA, Riederer SJ, Grimm RC, Ehman RL, Felmlee JP, Jack CR, Jr. Prospective multiaxial motion correction for fMRI. Magn Reson Med. 2000;43:459-469.
Wong ST, Roos MS. A strategy for sampling on a sphere applied to 3d selective RF pulse design. Magn Reson Med. 1994;32:778-784.
Irarrazabal P, Nishimura DG. Fast three dimensional magnetic resonance imaging. Magn Reson Med. 1995;33:656-662.
Welch EB, Manduca A, Grimm RC, Ward HA, Jack CR, Jr. Spherical navigator echoes for full 3d rigid body motion measurement in MRI. Magn Reson Med. 2002;47:32-41.
Welch EB, Manduca A, Grimm RC, Jack CR, Jr. Interscan registration using navigator echoes. Magn Reson Med. 2004;52:1448-1452.
Li S, Dardzinski BJ, Collins CM, Yang QX, Smith MB. Three-dimensional mapping of the static magnetic field inside the human head. Magn Reson Med. Nov. 1996;36(5):705-14.
Collins CM, Yang B, Yang QX, Smith MB. Numerical calculations of the static magnetic field in three-dimensional multi-tissue models of the human head. Magn Reson Imaging. Jun. 2002;20(5):413-24.
Romeo F, Hoult D.I. Magnet field profiling: analysis and correcting coil design. Magn. Reson. Med. Mar. 1984;1(1):44-65.
Prammer MG, Haselgrove, J.C., Shinnar, M., Leigh, J.S. A new approach to automatic shimming. J Magn Reson 1988; 77:40-52.
Webb P., Macovski A."Rapid, fully automatic, arbitrary volume in vivo shimming" Magn Reson Med. 1991; 20 (1), 113-22.
Schneider E., Glover G."Rapid in vivo proton shimming" Magn Reson Med 1991;18(2), 335-47.

Hu, J., Javaid T., Arias-Mendoza F., Liu Z., Mc Namara R., and Brown T.R., "A fast, reliable, automatic shimming procedure using 1H chemical—shift imaging spectroscopy" J Magn Reson 1995; 108, 213-219.
Reese TG, Davis, T.L., Weisskoff,R.M. Automated shimming at 1.5T using echo planar image frequency maps. J Magn Reson Imaging 1995; 5(6):739-745.
Wilson JL, Jezzard P. Utilization of an intra-oral diamagnetic passive shim in functional MRI of the inferior frontal cortex. Magn Reson Med 2003; 50(5):1089-1094.
Cusack R, Russell B, Cox SM, De Panfilis C, Schwarzbauer C, Ansorge R. An evaluation of the use of passive shimming to improve frontal sensitivity in fMRI. Neuroimage 2005; 24(1):82-91.
Hsu JJ, Glover GH. Mitigation of susceptibility-induced signal loss in neuroimaging using localized shim coils. Magn Reson Med 2005; 53(2)243-248.
Hillenband DF, Lo, K-M, Punchard WFB, Reese TG, Starewicz PM. "High-order shimming: a simulation study of the effectiveness of competing methods, using an established susceptibility model of the human head", Applied Magnetic Resonance, Appl Magn Reson 2005; 29(1): 39-64.
De Graaf R.A., Brown P.B., McIntyre S., Rothman D.L., Nixon T.W. "Dynamic shim updating (DSU) for multislice shim acquisition" Magn. Reson. Med. 2003; 49(3), 409-16.
Kim D.H., Adalsteinsson E., Glover G.H., Spielman D.M. "Regularized high-order in vivo shimming" Magn Reson Med. 2002; 48(4), 715-22.
Klassen L.M., Menon R.S., "Robust automated shimming technique using arbitrary mapping acquisition parameters (RASTAMAP)" Magn Reson Med 2004; 51(5), 881-7.
Blamire AM, Rothman DL, Nixon T. "Dynamic shim updating: a new approach towards optimized whole brain shimming." Magn Reson Med. 1996; 36(1) 159-65.
Zhao Y, Anderson AW, Gore JC. "Computer simulation studies of the effects of dynamic shimming on susceptibility artifacts in EPI at high field." J Magn Reson 2005; 173(1) 10-22.
Henry PG, van de Moortele PF, Giacomini E, Nauerth A, Bloch G. Field-frequency locked in vivo proton MRS on a whole-body spectrometer. Magn Reson Med. Oct. 1999;42(4):636-42.
Thiel T, Czisch M, Elbel GK, Hennig J. Phase coherent averaging in magnetic resonance spectroscopy using interleaved navigator scans: compensation of motion artifacts and magnetic field instabilities. Magn Reson Med. Jun. 2002;47(6):1077-82.
Ebel A, Maudsley AA. Detection and correction of frequency instabilities for volumetric 1H echo-planar spectroscopic imaging. Magn Reson Med. Feb. 2005;53(2):465-9.
Golman K, in 't Zandt R, Thaning M. Real-time metabolic imaging. Proc Natl Acad Sci U S A. Jul. 25, 2006;103(30):11270-5.
Van Der Kouwe AJ, Benner T, Dale A. Real Real-Time Rigid Body Motion Correction and Shimming Using Cloverleaf Navigators. Magn Reson Med., Nov. 2006;56(5):1019-32.

* cited by examiner

MAGNETIC RESONANCE SPECTROSCOPY WITH REAL-TIME CORRECTION OF MOTION AND FREQUENCY DRIFT, AND REAL-TIME SHIMMING

REFERENCE TO RELATED APPLICATIONS

Applicant claims priority of U.S. Provisional Application No. 60/795,381, filed on Apr. 27, 2006 for SYSTEM AND METHODS FOR MAGNETIC RESONANCE SPECTROSCOPIC IMAGING WITH SPATIALLY RESOLVED FREQUENCY DRIFT CORRECTION INTEGRATED INTO THE WATER SUPPRESSION MODULE of Stefan Posse, Applicant herein.

FEDERALLY SPONSORED RESEARCH

The present invention was made with government support under Grant No. 1 R01 DA14178-01 awarded by the National Institutes of Health. As a result, the Government has certain rights in this invention.

BACKGROUND OF THE INVENTION

1. Technical Field of the Invention

This invention relates to localized magnetic resonance spectroscopy (MRS) and to magnetic resonance spectroscopic imaging (MRSI) of the proton NMR signal, specifically to a magnetic resonance spectroscopy (MRS) method to measure a single volume of interest and to a magnetic resonance spectroscopic imaging method with at least one spectral dimension and up to three spatial dimensions. MRS and MRSI are sensitive to movement of the object to be imaged and to frequency drifts during the scan that may arise from scanner instability, field drift, respiration, and shim coil heating due to gradient switching. Inter-scan and intra-scan movement leads to line broadening and changes in spectral pattern secondary to changes in partial volume effects in localized MRS. In MRSI movement leads to ghosting artifacts across the entire spectroscopic image. For both MRS an MRSI movement changes the magnetic field inhomogeneity, which requires dynamic reshimming. Frequency drifts in MRS and MRSI degrade water suppression, prevent coherent signal averaging over the time course of the scan and interfere with gradient encoding, thus leading to a loss in localization. It is desirable to measure object movement and frequency drift and to correct object motion and frequency drift without interfering with the MRS and MRSI data acquisition.

2. Description of the Prior Art

High-Speed MR Spectroscopic Imaging:

High speed MRSI integrates spatial encoding modules into the spectral acquisition. We have developed Proton-Echo-Planar-Spectroscopic-Imaging (PEPSI) which employs echo-planar readout gradients to accelerate spatial encoding times by more than one order of magnitude as compared to conventional techniques to measure 2-dimensional metabolite distributions at short TE and 3-dimensional metabolite distributions (1,2). PEPSI has also been employed for time-resolved metabolic imaging to dynamically map lactate concentrations during respiratory and metabolic challenges (3,4), to characterize metabolic dysfunction during sodium-lactate infusion in patients with panic disorder (5) and to map multiplet resonance in human brain at short echo time and high field strength (6). We have further increased the encoding speed of high-speed MRSI by combining Proton-Echo-Planar-Spectroscopic-Imaging (PEPSI) with parallel imaging to obtain up to 4-fold acceleration and measurement times of 16 s for a 32×32 matrix with TR 2 s (7) on a 4 Tesla scanner. This technology is particularly advantageous for 3-dimensional spatial mapping and further improvement in encoding efficiency enabled single-shot MRSI (8) in our laboratory.

Motion Detection and Correction

The first on-line prospective real-time methods used straight-line navigators to detect linear motion of organs in the chest (9). These techniques are not applicable in brain scans where rigid body motion in any arbitrary plane and along any axis is possible. In a series of papers, researchers at the Mayo Clinic describe the concepts of orbital and spherical navigators for prospective rigid body motion detection and correction. The orbital (circular) navigator enables the detection of rotation within the plane of the navigator and translations along multiple axes (10, 11). Ward et al. developed a real-time prospective motion correction scheme in which a set of three circular navigators is used to detect motion in all three planes (11). An iterative approach is taken to correct for the motion since the rotations may still be out of the plane of the navigators. The procedure is fairly time consuming and works best for rotations about the cardinal axes. The spherical navigator, first described by Wong and Irarrazabal (12,13) and implemented in a full 3D rigid body measurement application by Welch et al. (14), addresses the problem of off-axis rotations. One implementation of the spherical navigators requires 27 ms for acquisition of the navigator information. Costa et al. have described a 3D rigid body motion correction method using polar spherical navigators (15). By pre-rotating the baseline trajectory of the navigator, the iterations are avoided.

There are no published methods to detect and correct object movement during an ongoing MRS or MRSI scan. Motion correction can be applied post-acquisition using standard registration tools, but the low resolution of the MRSI scan limits the performance of this approach. It is possible to interleave volumetric high resolution MRI scans into the MRS or MRSI scan to detect and prospectively correct movement, but this approach requires additional signal excitation, which interferes with the signal excitation for the spectroscopic acquisition, leading to reduced sensitivity and possible instability in the MRS and MRSI data, and it reduces the temporal resolution of MRS and MRSI.

Compensation of Magnetic Field Inhomogeneity

Magnetic resonance spectroscopic imaging and localized spectroscopy in vivo suffer from microscopic and macroscopic magnetic field inhomogeneity that broaden spectral lines, reduce sensitivity and impair spectral fitting. This is one of the major limitations of MRS and MRSI in vivo. Conventional means of compensating such inhomogeneity include: (a) shimming, which is limited to low shim coils with spatial frequencies and therefore not very effective over large volumes (b) separate acquisition of multiple volumes with different shim settings, which is time consuming (c) increasing spatial resolution, which is very costly in terms of sensitivity and increases measurement time.

Inhomogeneity of the static magnetic field ($B_0$) can be as large as 6 parts-per-million (ppm) across the brain (16,17). These spatial nonlinearities of local gradients are an important limiting factor in volumetric MRSI studies. Higher order auto-shimming (HOAS) provided on most high-field scanners offers limited capability for correction of such imperfections. While all MR processes will benefit from improved shimming to some degree, specific regions of clinical interest, such as the frontal and medial-temporal brain regions, and acquisition techniques, such as MRSI, can be critically affected by shimming effectiveness. In the case of MRS and MRSI, shim state can adversely affect spectral line width, causing artifactual frequency shifts between voxels and decrease effectiveness of water suppression. Furthermore, poorly suppressed water signal can alias into regions of otherwise adequate water suppression as a result of subject motion or k-space undersampling, causing baseline artifact. Aliasing of residual water signals from regions outside of the volume of interest is particularly difficult to identify.

HOAS typically uses a collection of shim coils based on spherical harmonics or other spatial shapes (for a review, see (18)). These coils are powered by current-feedback amplifiers under the control of a user-addressable interface and analysis program. The corrective fields generated by the coils are of finite number, power and extent. Due to time constraints, HOAS attempts to converge to an optimum shim state analytically rather than iteratively, using field maps collected with the existing imaging capability (19-23). Progress in improving existing technique has focused on addressing the limits of the shimming hardware (24-29) and accuracy and stability of the analysis (30,31). However, for MRS and MRSI the performance of HOAS is still insufficient, in particular at high field.

To overcome large local disturbances in field homogeneity, several methods for correction have been proposed. The use of additional passive ferromagnetic shims in a cylindrical array, placed in close proximity to the human head, has been demonstrated (24). Mouthpieces containing diamagnetic shim material (passive shims) have been developed to enhance the $B_o$ homogeneity of the mesioinferior frontal lobes (25,26). Hsu and Glover (27) have taken a similar approach but have used a mouthpiece than contains an active shim coil. However, for clinical applications of spectroscopic imaging these approaches are not practical.

Extending the capability of the existing field coil design requires either more coils of higher order (28), or better control over the existing coils. To increase control, Blamire and colleagues (32) showed that a dynamic shim state, following the current acquisition slice, can improve the corrective power of the shim coils by reducing the spatial constraints on the shim state. Subsequent studies have further demonstrated its effectiveness (33). Dynamic shimming offers greater flexibility in compensating local magnetic field distortion, but applications are currently limited by the considerable hardware demands. However, the clinical manufacturers have identified dynamically switched higher order shims as an important advance and have started product development. It is thus foreseeable that switching higher order shims will become clinical routine.

Frequency Drift Correction

MRS and MRSI are sensitive to frequency drifts during the scan that may arise from scanner instability, field drift, respiration, and shim coil heating due to gradient switching. Frequency drifts degrade water suppression, prevent coherent signal averaging over the time course of the scan and interfere with gradient encoding, thus leading to a loss in localization (34-36). Ebel et al. published a method that collects an additional MRSI data set interleaved into the conventional MRSI data acquisition to detect and correct frequency drifts (36). However, this approach is associated with additional signal excitation, which interferes with the signal excitation for the spectroscopic acquisition, leading to reduced sensitivity and possible instability in the MRSI data, and it reduces the temporal resolution of MRSI. It is desirable to measure this frequency shift and to correct the frequency drift without interfering with the MRSI data acquisition. Ideally, this frequency measurement should be performed in small volumes, since this reduces the effect of magnetic field inhomogeneity and makes the frequency measurement more precise. In addition, it is desirable to simultaneously measure the frequency drift in multiple volumes, since the frequency drift may vary in space [34], e.g. due to breathing or due to gradient drift.

U.S. Pat. No. 6,552,539 discloses a method of correcting resonance frequency variation and MRI apparatus. A method of correcting a resonance frequency variation and an MRI apparatus both capable of handling all frequency drifts including a frequency drift whose time change is slow, a frequency drift in a slice direction and a frequency drift whose time change is fast. An amount of a resonance frequency variation is measured, the frequency variation is corrected when an amount of the resonance frequency variation is smaller than a threshold value, and the amount of the resonance frequency variation is not stored. On the other hand, when the amount of the resonance frequency variation is not smaller than the threshold value, the amount of the resonance frequency variation is stored and correction operation is made based thereon later. This method is not applicable to MRS and MRSI.

U.S. Pat. No. 5,166,620 discloses an NMR frequency locking circuit. An NMR locking mechanism for use with not only electromagnets, superconducting magnets and permanent magnets, but also with ultrahigh energy product magnets such as neodynium. The circuit utilizes a single conversion superheterodyne receiver with a phase locked loop that forms a locking mechanism that depends upon a variable frequency. The resonant frequency of the nuclei is compared to a variable excitation frequency which is adjusted to maintain a control frequency with one unique value of the control frequency being zero at lock. This method is suitable for compensating drifts of the main magnetic field, but it is not suitable to compensate movement or changes in magnetic field inhomogeneity.

High-speed MR spectroscopic imaging has important applications.

The development of hyperpolarized MRI agents presents both unprecedented opportunities and new technical challenges. In particular, with signal-to-noise ratio (SNR) enhancements on the order of the 10000-fold, dynamic nuclear polarization of metabolically active substrates (e.g., 13C-labeled pyruvate or acetate) theoretically permits in vivo imaging of not only the injected agent, but also downstream metabolic products. This feature of hyperpolarized MR spectroscopy (MRS) provides investigators a unique opportunity to non-invasively monitor critical dynamic metabolic processes in vivo under both normal and pathologic conditions. Important applications include tumor diagnosis and treatment monitoring, as well as assessment of cardiac function. In studies using hyperpolarized samples, the magnetization decays toward its thermal equilibrium value and is not recoverable. Therefore, fast spectroscopic imaging acquisition schemes are important.

A recent study by Golman et al. (37) described real-time metabolic imaging. NMR spectroscopy has until now been the only noninvasive method to gain insight into the fate of pyruvate in the body, but the low NMR sensitivity even at high field strength has only allowed information about steady-state conditions. The medically relevant information about the distribution, localization, and metabolic rate of the substance during the first minute after the injection has not been obtainable. Use of a hyperpolarization technique has enabled 10-15% polarization of 13C1 in up to a 0.3 Mpyruvate solution. i.v. injection of the solution into rats and pigs allows imaging of the distribution of pyruvate and mapping of its major metabolites lactate and alanine within a time frame of 10 s. Hyperpolarized MRS is currently being developed by major manufacturers and expected to be of considerable commercial value.

MR spectroscopic imaging in moving organs, like the heart or the breast, is sensitive to movement artifact that results in blurring of the image. Gating to the heart beat is frequently used to reduce motion artifact, but this reduces data acquisition efficiency. Simultaneous synchronization to respiration may be required to further reduce motion artifacts, which additionally reduces data acquisition efficiency. Gating in the presence of irregular heart beat introduces variability in repetition time that results in non steady-state signal intensity and distortion of the image encoding process. Image registration during post-processing is challenging due to the highly nonlinear movement pattern within the chest. High-speed spectroscopic imaging acquisition schemes considerably reduce motion sensitivity.

MR spectroscopic imaging in organs, like the brain, is sensitive to localized signal fluctuations due to blood pulsation or other physiological movement mechanisms (e.g. CSF movement) that results in blurring of the image. Gating to the rhythm of the physiological fluctuation (e.g. heart beat) can be used to reduce this artifact, but this reduces data acquisition efficiency. Gating in the presence of irregular heart beat introduces variability in repetition time that results in non steady-state signal intensity and distortion of the image encoding process. Therefore, fast spectroscopic imaging acquisition schemes are important.

This method is also applicable to spatial mapping chemical reactions for applications in material science and biology. For example, the spatial evolution of a chemical chain reaction could be observed. Such reactions are typically very fast and fast spectroscopic imaging acquisition schemes are thus important to avoid blurring of the spectroscopic images.

SUMMARY OF THE INVENTION

The innovation consists of a modification of the water suppression module in a proton MRS or MRSI sequence to simultaneously measure and correct the frequency drift, the change in magnetic field inhomogeneity in the volume of interest, the object movement, and to suppress the water signal. The water signal that is excited within the water suppression module originates from the entire object seen by the RF coil and the corresponding water spectrum is broadened by magnetic field inhomogeneity, which reduces sensitivity to measuring small frequency shifts. By inserting between the water suppression RF pulse and the dephasing gradient pulses either a phase sensitive MRI encoding module, or a 1D, 2D or 3D high-speed MRSI encoding module with simultaneous acquisition of the decaying water signal it is possible to measure frequency drift, magnetic field inhomogeneity and object movement. The information in this navigator water signal is used to dynamically change the synthesizer frequency of the scanner, the shim settings and to shift the encoded k-space. In the preferred implementation this information is computed in real-time during the ongoing scan and via feeback loop downloaded to the acquisition control unit to update the aforementioned parameters before the subsequent data acquisition. In the most basic implementation of the method a train of cyclically inverted readout gradients is applied immediately after the water suppression RF pulse and before the water suppression crusher gradient pulse to measure and spatially encode the decaying water signal. This train of readout gradients simultaneously encodes one spatial direction and spectral information. Crusher gradients are applied at the end of the readout gradient train to dephase the residual water signal.

It is an object of the present invention to enable magnetic resonance spectroscopic imaging with real-time motion and frequency drift correction.

It is another object of the present invention to provide an magnetic resonance spectroscopic imaging apparatus with real-time motion and frequency drift correction:

These and significant other advantages of the present invention will become clear to those skilled in this art by careful study of this description, accompanying drawings and claims.

DETAILED DESCRIPTION OF THE PRESENT INVENTION

Figure 1:
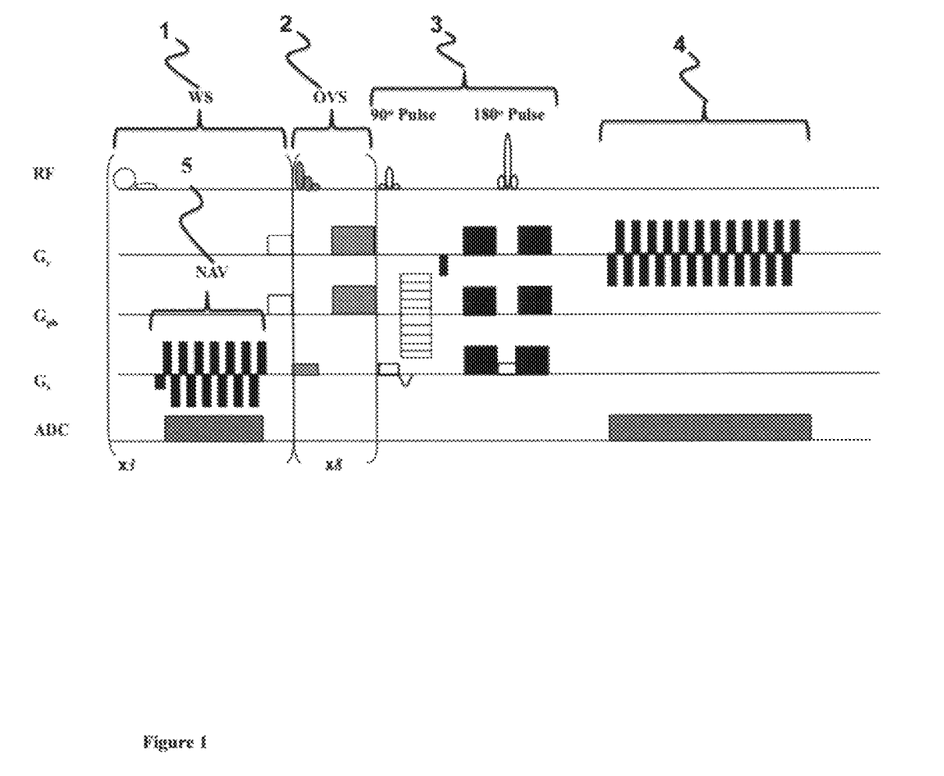
FIG. 1 shows a PEPSI pulse sequence with water suppression (WS) that incorporates navigator signal collection (NAV), outer volume suppression (OVS), the spin echo excitation module and the echo-planar readout module. Data are collected in blocks during each of the cyclically inverted readout gradients ($G_r$).

The water signal is deliberately suppressed in localized proton MRS and proton MRSI. This invention spatially-spectrally encodes this signal, which is available immediately after the water excitation pulse, using gradient encoding before dephasing the MR signal with crusher gradients. In this location within the pulse sequence, the magnetization available for excitation will be unaffected, and the impact on water suppression and pulse sequence timing will be minimal. FIG. 1 shows a PEPSI pulse sequence (1,2) with water suppression (WS) 1, outer volume suppression (OVS) 2, the spin echo excitation module 3 and the echo-planar readout module 4 to measure the spectroscopic signal. Data are collected in blocks during each of the cyclically inverted readout gradients ($G_r$). The invention involves the insertion of a navigator module 5 into the water suppression (WS) module between the water suppression RF pulse and the dephasing gradient pulses. The navigator module consists of a spatial or spatial-spectral gradient encoding module and simultaneous acquisition of the decaying water signal. This gradient encoding module may consist of a phase sensitive MRI encoding module, or a 1D, 2D or 3D high-speed MRSI encoding module to measure spatially resolved amplitude and phase of the decaying water signal. The figure depicts a spatial-spectral gradient encoding module that simultaneously encodes spatial information along the slice direction and spectral information. This navigator module may be inserted into a single or into multiple consecutive water suppression modules. This modification is not specific to the PEPSI pulse sequence, but can be applied to any localized spectroscopy and spectroscopic imaging pulse sequence that contains water suppression modules. Furthermore, two or more sets of navigators could be collected in quick succession in consecutive water suppression modules to estimate intra-scan frequency drifts, intra-scan changes in magnetic field inhomogeneity and intra-scan movement.

Figure 2:
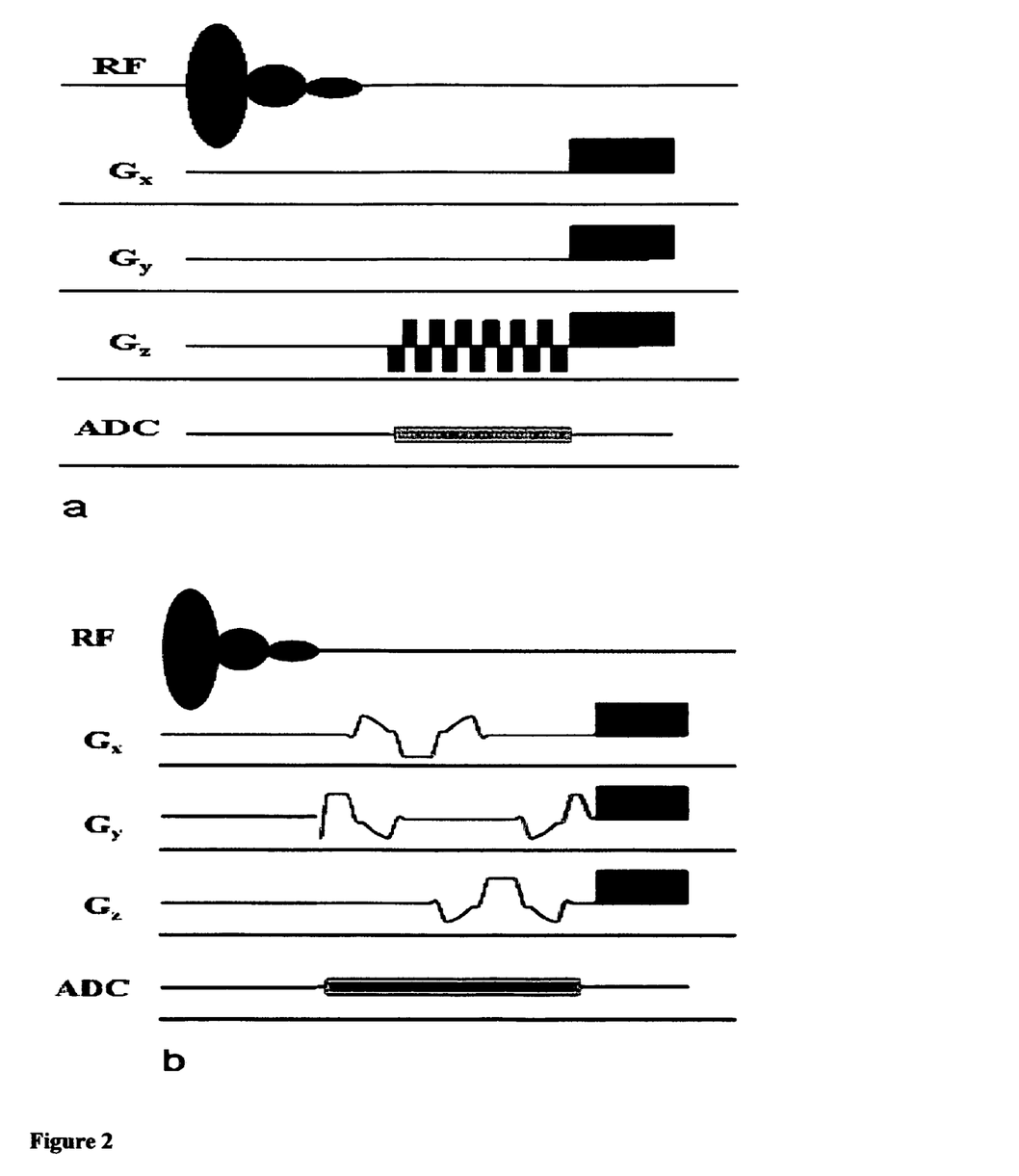
FIG. 2 shows examples of the integration of data encoding modules into the water suppression module: (a) an MRSI readout module used in the PEPSI sequence, (b) a cloverleaf navigator module developed by van der Kouwe (38).
Figure 3:
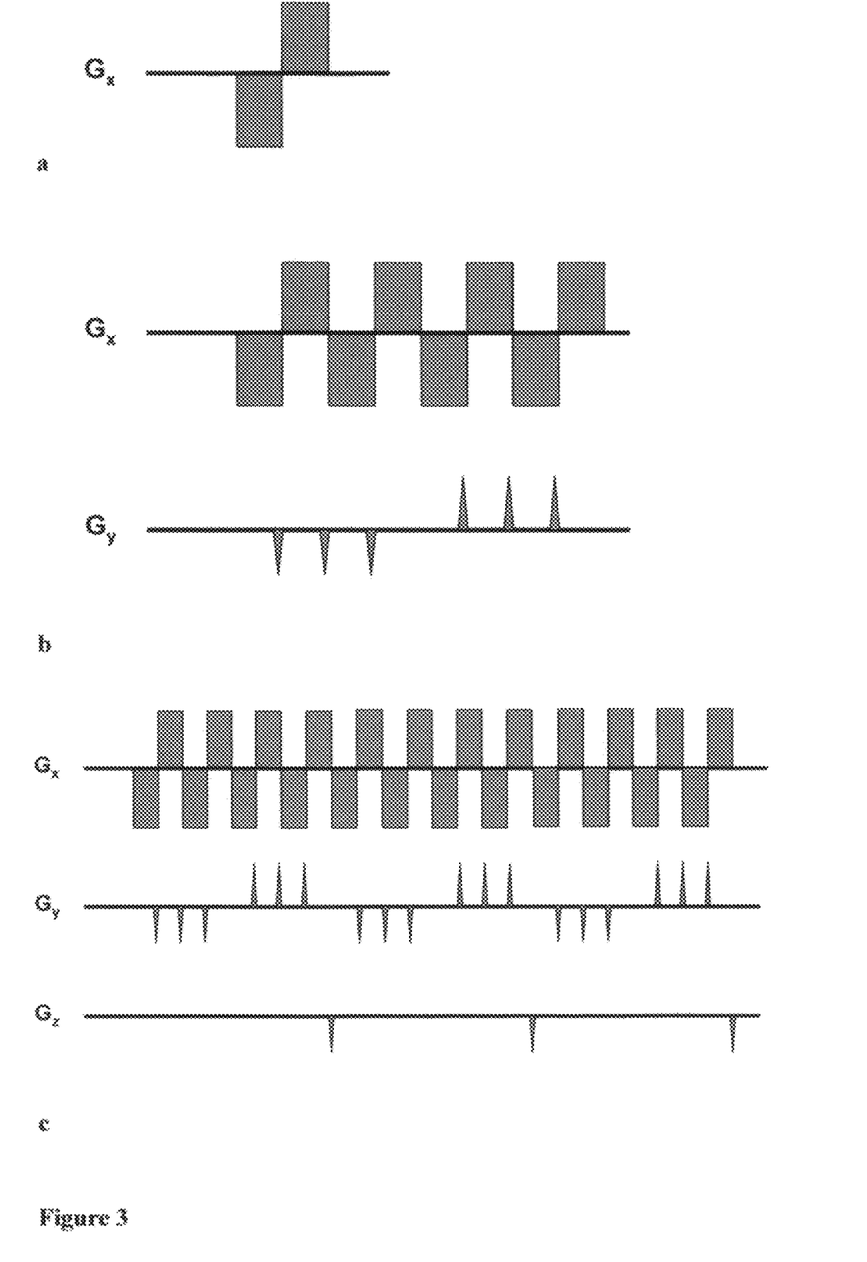
FIG. 3 illustrates examples of encoding modules but not limited to these: (a) 1D encoding (b) 2D single-shot encoding (c) 3D single shot encoding.
Figure 4:
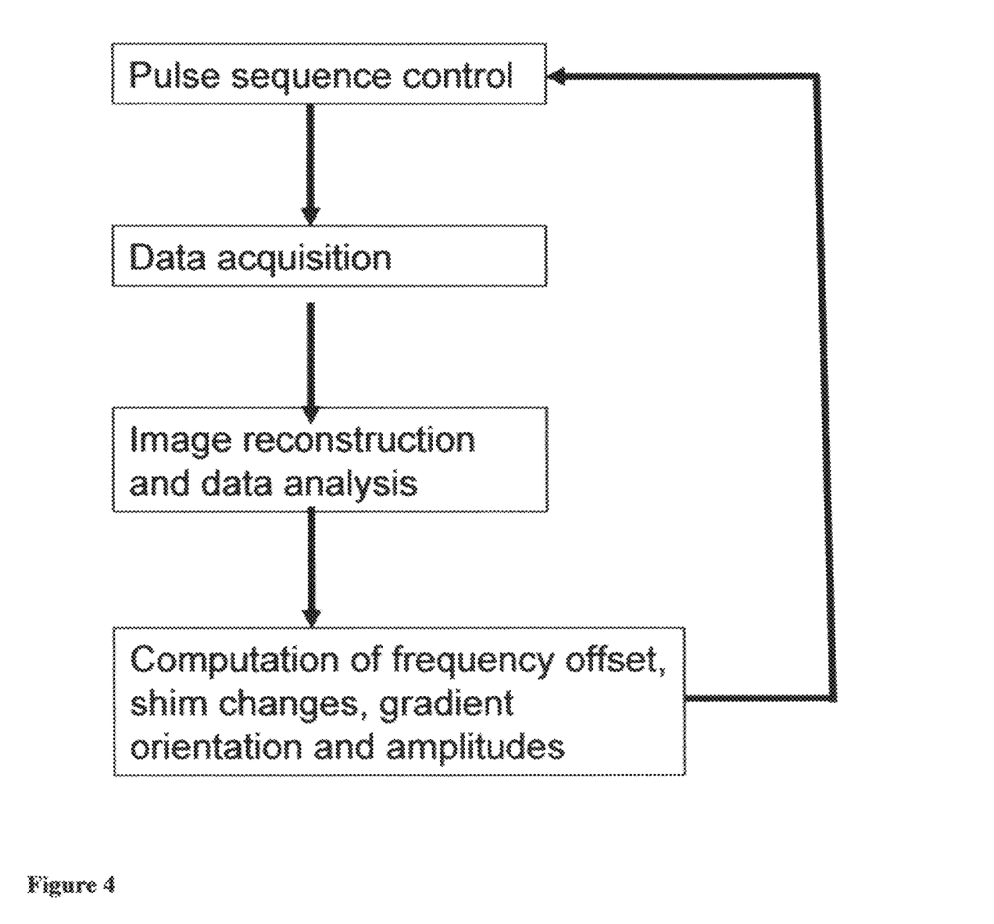
FIG. 4 shows a flow chart of the feedback loop to dynamically change the frequency of the RF subsystem, the shim settings and the magnetic field gradient amplitudes and orientations to change the orientation of the k-space grid during the ongoing scan.

FIG. 2 shows examples of the implementation of data encoding modules into the water suppression. FIG. 2a shows a 1-dimensional spatial encoding module based on the PEPSI sequence. The duration of the readout gradient train determines the spectral resolution. It is limited by the total duration of the water suppression module and the duration of the water suppression RF pulse. The duration of each individual readout gradient determines the spectral width (1,2). Repetition of this measurement in consecutive water suppression modules enables extrapolation of intra-scan frequency drifts, shim changes and movement. Other possible gradient modules include phase sensitive MRI encoding module, or a 1D, 2D or 3D high-speed MRSI encoding module.

In the human brain magnetic field inhomogeneities are most prominent along the z-direction. Using a z-gradient to spatially resolve the magnetic field inhomogeneities will thus improve the detection of small frequency shifts that may vary between individual axial slices. In general the readout module should be applied along the direction with greatest magnetic field inhomogeneity. Further improvement in the precision of the frequency measurement can be achieved by encoding 2D or 3D space, simultaneously with spectral information to obtain column- or voxel-resolved frequency information. These 2D and 3D encoding modules are either applied in a single shot and repeated rapidly to encode spectral information, or applied across multiple acquisition steps of the main MRSI sequence. Measurement of the spatially resolved amplitude and frequency of the navigator signal excited by the water suppression RF pulse enables_computation of the mean frequency offset and the spatially resolved frequency as a measure of magnetic field distribution in the object being imaged, which can be corrected by changing the synthesizer frequency and the shim coil current settings using standard frequency tuning and automatic shimming methods available on clinical MRI scanners. This measurement also enables determination of the position of the object within the MRI scanner. Changes of the spatially resolved amplitude and frequency of the navigator signal between measurements enables computation of changes in magnetic field inhomogeneity inside the object and movement (displacement and rotation) of the object between measurements (inter-scan changes). Repeated measurement of spatially resolved amplitude and frequency of the navigator signals in consecutive water suppression modules enables extrapolation of changes in magnetic field inhomogeneity inside the object and movement of the object at consecutive time points during the echo-planar readout of the spectroscopic signal (intra-scan changes). These measurements are preferably performed using parallel imaging with an RF coil array, which employs k-space undersampling to reduce the duration of the spatial-spectral encoding module inserted into the water suppression module. Parallel imaging data acquisition and reconstruction using GRAPPA and SENSE are available on clinical MRI scanners.

FIG. 2b shows the cloverleaf navigator, which has been designed and tested for use in gradient echo imaging sequences by van der Kouwe et al (38). Every navigator scan will not be in the steady-state as in the FLASH sequence. The non steady-state behavior of the navigators across the train of echoes can be modeled, mapped and corrected. Early experience with a conventional MRSI sequence suggests that even without correction, reasonable though biased estimates result. The bias will be reduced by correcting for the non-steady-state. Second, if the rotation estimates are biased, averaging will not reduce the bias. If this appears to be a problem, we will lengthen the arc segments of the navigators (e.g. to 180 degrees) and/or include navigators with different radii in the train (thus interrogating the object at different resolutions and improving the rotation estimates). The accuracy of the translation estimates from the navigators may also be compromised by field drifts. Zeroth order offsets in the B0 field appear as a linear phase roll across the navigator readout that is independent of the applied gradient. Improved phase estimation will be obtained by using multiple repetitions of the cloverleaf navigator within a water suppression module. We have observed that instantaneous frequency estimates from cloverleaf navigators embedded in gradient echo imaging sequences have a noise component with a variance of less than 1 Hz (38). Since several repeated estimates will be made at regular intervals in the spectroscopy sequence, and assuming the drift estimates are unbiased, the accuracy can be increased by low-pass filtering to well below the target resolution of 1 Hz.

Magnetic field inhomogeneity information can be collected using more fully encoded 2D or 3D spatial MRSI modules, or 3D or 3D phase sensitive MRI modules.

The frequency drift correction, required shim changes to compensate motion related (or due to other factors) changes in magnetic field inhomogeneity and required changes in the magnetic field gradient orientation to compensate movement will be computed online and downloaded into the pulse sequence to enable online correction of all transmit RF pulse frequencies, gradient amplitudes and orientations and the receiver frequency offset. As mentioned above, frequency drift, magnetic field inhomogeneity changes inside the object and movement of the object may be extrapolated using multiple navigator signals in consecutive water suppression modules. The receiver frequency offset, the shim settings and the magnetic field gradient orientation may be adjusted in real-time to compensate the extrapolated frequency drift, to minimize the magnetic field inhomogeneity change inside the object and to correct the effects of movement of the object during the echo-planar readout of the spectroscopic signal. Most clinical scanners provide a convenient mechanism (e.g. used in the Siemens PACE motion correction implementation in the product sequences (1) for rapidly feeding back corrections to the gradient and RF subsystems in a closed-loop time of less than 5 ms. On a Siemens scanner this can be carried out using the Image Calculation Environment (postprocessing software) of the scanner. Online movement correction may be performed using the product PACE method implemented in the ICE reconstruction program (38).

Figure 5:
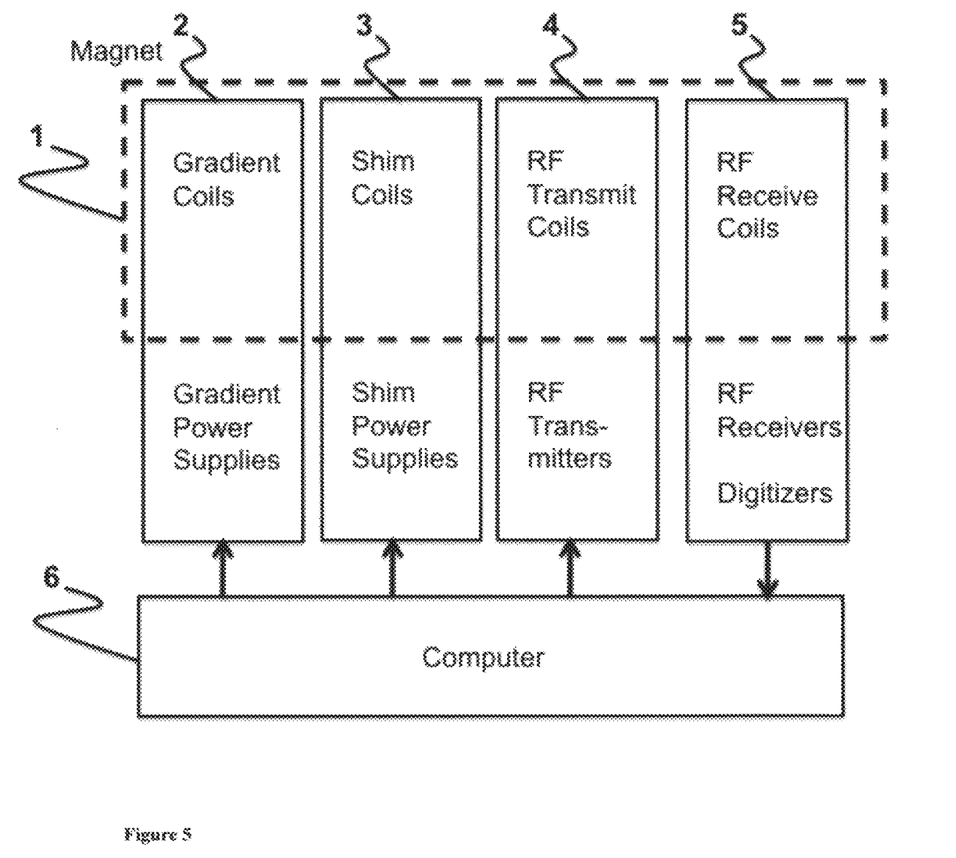
FIG. 5 shows the arrangement of an MRI apparatus, which is used in this invention. The MRI apparatus includes a computer that generates the MR pulse sequence with the modified water suppression module, measures and reconstructs the navigator MR signals, and controls the components of the MRI apparatus to change the frequency of the RF subsystem, the shim settings and the magnetic field gradient amplitudes and orientations.

This MRS and MRSI methodology is implemented using a conventional MRI apparatus depicted in FIG. 5. Briefly, the apparatus consists of a magnet 1 to generate a static magnetic field $B_0$, gradient coils and power supplies 2 to generate linear magnetic field gradients along the X, Y and Z axes, shim coils and shim power supplies 3 to generate higher order magnetic field gradients, single or multiple radiofrequency (RF) transmit coils and RF transmitter 4 to generate an RF field, single or multiple RF receiver coils forming an array, RF receivers and digitizers 5 to measure the received RF field, and a computer 6 to generate the pulse sequence, to measure and reconstruct the MR signals and to control the components of the MRI apparatus. The computer performs real-time-data analysis to measures the spatially resolved amplitude, frequency and phase of the navigator signals measured in the water suppression step and changes thereof between measurements. Based on these measurements it computes the mean frequency offset and magnetic field inhomogeneity inside the object, the position of the object and changes thereof between measurements, using linear or nonlinear extrapolation. Based on these results of these extrapolations the computer modulates the pulse sequence control device, and applies changes in transmitter and receiver frequency, shim settings, and gradient amplitudes and orientations during spatial prelocalization and during the echo-planar readout of the spectroscopic signal.

The invention claimed is:

1. An MRI method that permits collecting a localized spectrum and a spectroscopic image with one spectral dimension and up to three spatial dimensions using an NMR apparatus comprising:
    application of RF pulses and gradients to excite nuclear spins in a circumscribed region;
    application of gradient pulses to localize signals and encode k-space wherein;
    a magnetic resonance spectroscopy pulse sequence and a magnetic resonance spectroscopic imaging pulse sequence comprises the sequential steps of applying one or more water suppression modules, spatial prelocalization and signal readout in the presence of spatial-spectral encoding gradients that encode up to 3 spatial dimensions and 1 spectral dimension; a spatial-spectral measurement within said water suppression modules comprising the three sequential steps of (a) applying a radio frequency pulse that excites a water signal, (b) measurement of said water signal in the presence of spatial or spatial-spectral encoding gradients, and (c) applying gradients to dephase said water signal; reception of an NMR signal; and wherein the water suppression step additionally contains a measurement of the excited water signal in the presence of spatial-spectral encoding gradients that encode up to 3 spatial dimensions and 1 spectral dimension, and
    reconstruction of spectroscopic data and spectroscopic images.

2. An MRI method according to claim 1, further comprising:
    measurement of the spatially resolved amplitude, frequency and phase of said excited water signal in said water suppression step and changes thereof between pulse sequence repetitions; and
    computation of the position of said object in said water suppression step and changes thereof between pulse sequence repetitions.

3. An MRI method according to claim 2, further comprising:
    measurement of the changes in displacement and rotation of said object in consecutive repetitions of said water suppression step to extrapolate changes in the displacement and rotation of said object at consecutive time points during said signal readout step.

4. An MRI method according to claim 3, further comprising:
    real-time correction of said displacements and rotations.

5. An MRI method according to claim 4, further comprising:
    acceleration of spatial-spectral encoding in said water suppression modules using partial parallel imaging with radiofrequency array coils.

6. An MRI method according to claim 2, further comprising:
    measurement of changes in spatially resolved frequency in said object in consecutive repetitions of said water suppression step to extrapolate changes in spatially resolved frequency in said object at consecutive time points during said signal readout step.

7. An MRI method according to claim 6, further comprising:
    real-time correction of the mean of said frequency drifts using different receiver frequency offsets at consecutive time points during said signal readout step.

8. An MRI method according to claim 7, further comprising:
    acceleration of spatial-spectral encoding in said water suppression modules using partial parallel imaging with radiofrequency array coils.

9. An MRI method according to claim 6, further comprising:
    computation of changes in linear gradients and shim gradients that minimize the extrapolated magnetic field inhomogeneity in said object at consecutive time points during said signal readout step, and real-time magnetic field inhomogeneity correction applying said changes in linear gradients and shim gradients at consecutive time points during said signal readout step.

10. An MRI method according to claim 9, further comprising:
    acceleration of spatial-spectral encoding in said water suppression modules using partial parallel imaging with radiofrequency array coils.

11. An MRI apparatus that permits collecting a spectroscopic image with one spectral dimension and up to three spatial dimensions comprising:
    an RF pulse transmitting device to excite nuclear spins in a circumscribed region;
    a gradient pulse application device to localize signals and encode k-space;
    an NMR signal receiving device;
    a spatial-spectral data collection, reconstruction and storage device;
    a pulse sequence control device to generate a magnetic resonance spectroscopy pulse sequence and a magnetic resonance spectroscopic imaging pulse sequence comprising the sequential steps of water suppression, spatial prelocalization and signal readout in the presence of spatial-spectral encoding gradients that encode up to 3 spatial dimensions and 1 spectral dimension, wherein the water suppression step additionally contains a measurement of the excited water signal in the presence of spatial-spectral encoding gradients that encode up to 3 spatial dimensions and 1 spectral dimension, said measurement being inserted between the water suppression radiofrequency pulse and the dephasing gradients of the water suppression step;
    containing a real-time-data analysis device that measures the spatially resolved amplitude, frequency and phase of said excited water signal in said water suppression step and changes thereof between measurements, and computes the mean frequency offset and magnetic field inhomogeneity in said object, the position of said object and changes thereof between measurements; and
    a pulse sequence control device that consists of a real-time data analysis device, a real-time decision device and a feedback device to modulate the pulse sequence control device, and that applies changes in transmitter and receiver frequency, shim settings, and gradient amplitudes and orientations during said spatial prelocalization and signal readout steps.

12. A magnetic resonance spectroscopic imaging apparatus according to claim 11, further comprising:
multiple consecutive repetitions of said water suppression step and a device that extrapolates displacement and rotation of said object, mean frequency drift and change in magnetic field inhomogeneity in said object at consecutive time points during said signal readout step by comparing the currently acquired data with the data acquired in the previous repetitions of the water suppression step.

13. A magnetic resonance spectroscopic imaging apparatus according to claim 12, further comprising:
a decision device that determines the change in RF subsystem frequency, gradient subsystem amplitudes, and shim settings by minimizing said extrapolated displacement and rotation of said object, said mean frequency drift and change in magnetic field inhomogeneity in said object at consecutive time points during said signal readout step.

14. A magnetic resonance spectroscopic imaging apparatus according to claim 13, further comprising:
a real-time feedback-loop that accomplishes said changes in said RF subsystem frequency, gradient subsystem amplitudes, and shim settings during said signal readout step.

* * * * *